United States Patent [19]
Riner

[11] Patent Number: 5,261,881
[45] Date of Patent: Nov. 16, 1993

[54] NON-REUSABLE DISPENSING APPARATUS

[75] Inventor: Robert M. Riner, Modesto, Calif.

[73] Assignee: R. Myles Riner, M.D., Professional Corporation, Modesto, Calif.

[21] Appl. No.: 848,654

[22] Filed: Mar. 9, 1992

Related U.S. Application Data

[63] Continuation of Ser. No. 500,549, Mar. 28, 1990, abandoned.

[51] Int. Cl.$^5$ .............................................. A61M 5/00
[52] U.S. Cl. ................................ 604/110; 604/212; 604/215; 604/213; 128/919; 222/95; 222/107
[58] Field of Search ............... 604/110, 187, 192, 197, 604/200, 201, 212–217; 128/919; 222/92, 95, 107

[56] References Cited

U.S. PATENT DOCUMENTS

| | | | |
|---|---|---|---|
| 1,687,502 | 10/1928 | Marcy | 604/192 |
| 2,552,100 | 5/1951 | Leonetti | 604/192 |
| 2,618,263 | 11/1952 | Lakso et al. | 604/192 |
| 2,687,727 | 8/1954 | Lawshe | 604/204 |
| 2,722,257 | 11/1955 | Lockhart . | |
| 2,744,527 | 5/1956 | Barret et al. . | |
| 2,757,671 | 8/1956 | Haafkens . | |
| 2,862,496 | 12/1958 | Hassler et al. | 604/212 |
| 2,864,368 | 12/1958 | Senger | 604/200 |
| 2,911,972 | 11/1959 | Elinger | 604/216 |
| 2,923,296 | 2/1960 | Adams et al. | 604/215 X |
| 3,128,920 | 4/1964 | Volckening et al. . | |
| 3,192,925 | 7/1965 | Cunningham | 604/192 X |
| 3,204,835 | 9/1965 | Michel . | |
| 3,461,868 | 8/1969 | Palich | 604/192 |
| 3,524,537 | 8/1970 | Winter | 606/214 X |
| 3,736,933 | 6/1973 | Szabo | 604/212 X |
| 3,989,045 | 11/1976 | Van Eck . | |
| 4,022,206 | 5/1977 | Hilleman et al. | 604/197 |
| 4,159,718 | 7/1979 | Bower | 604/212 |
| 4,282,986 | 8/1981 | af Ekenstam et al. | 222/1 |
| 4,548,601 | 10/1985 | Lary | 604/204 |
| 4,883,473 | 11/1989 | Thomas | 604/217 |
| 4,955,871 | 9/1990 | Thomas | 604/217 |

FOREIGN PATENT DOCUMENTS

| | | | |
|---|---|---|---|
| 0553848 | 1/1960 | Belgium | 604/192 |
| 0310227 | 4/1989 | European Pat. Off. | 604/110 |
| 2359614 | 2/1978 | France | 604/192 |
| 0578808 | 7/1958 | Italy | 604/200 |

Primary Examiner—C. Fred Rosenbaum
Assistant Examiner—Mark O. Polutta
Attorney, Agent, or Firm—Worrel & Worrel

[57] ABSTRACT

A dispensing apparatus comprising a container adapted to house a fluid to be dispensed in sealed relation; an exposing member borne by the container for exposing the fluid for dispensing from the container through an opening; and a mount borne by the container adjacent to the exposing member operable to secure a needle or the like, through which the fluid can be passed, in fluid transferring relation to the opening of the container.

6 Claims, 2 Drawing Sheets

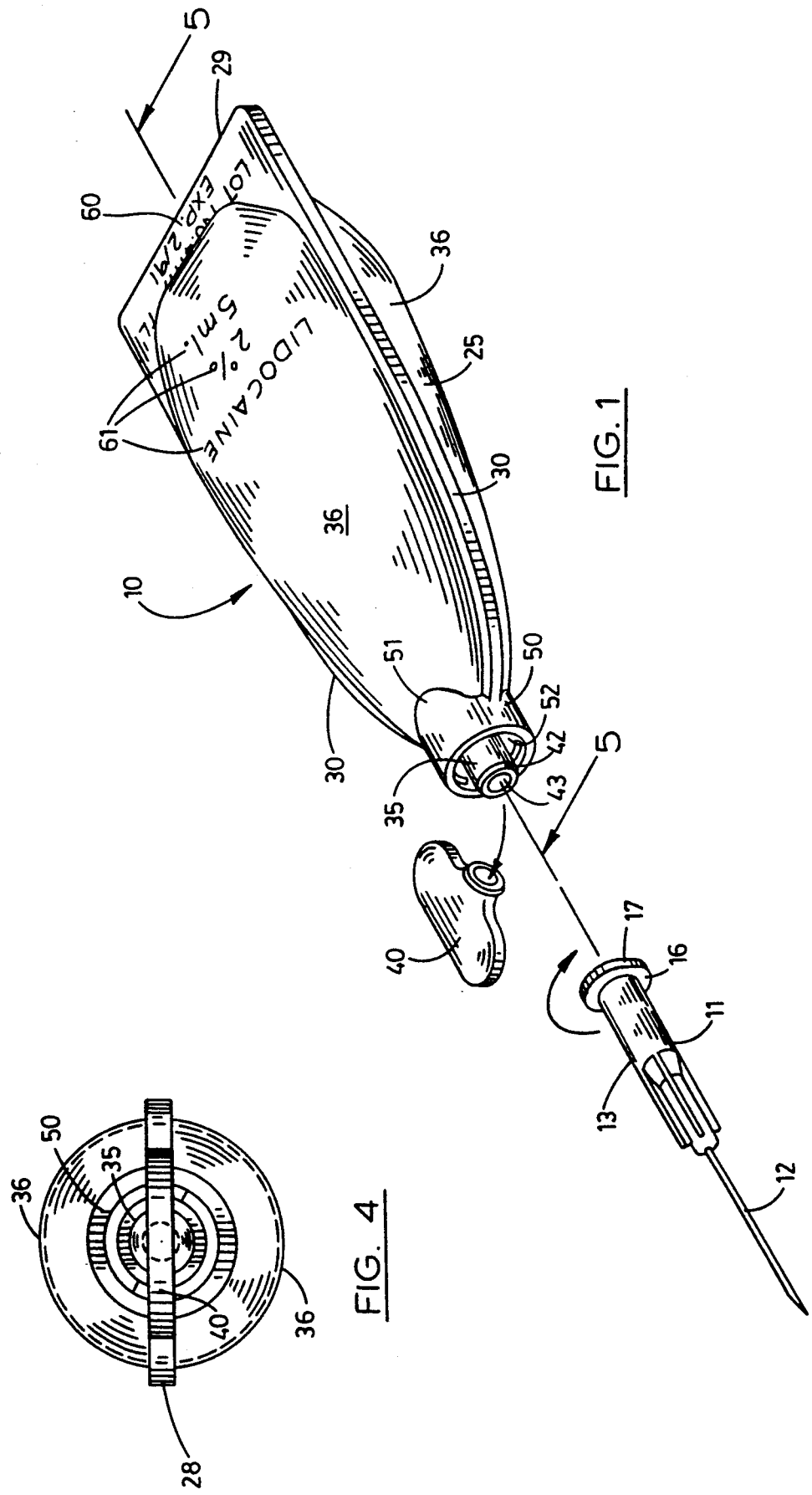

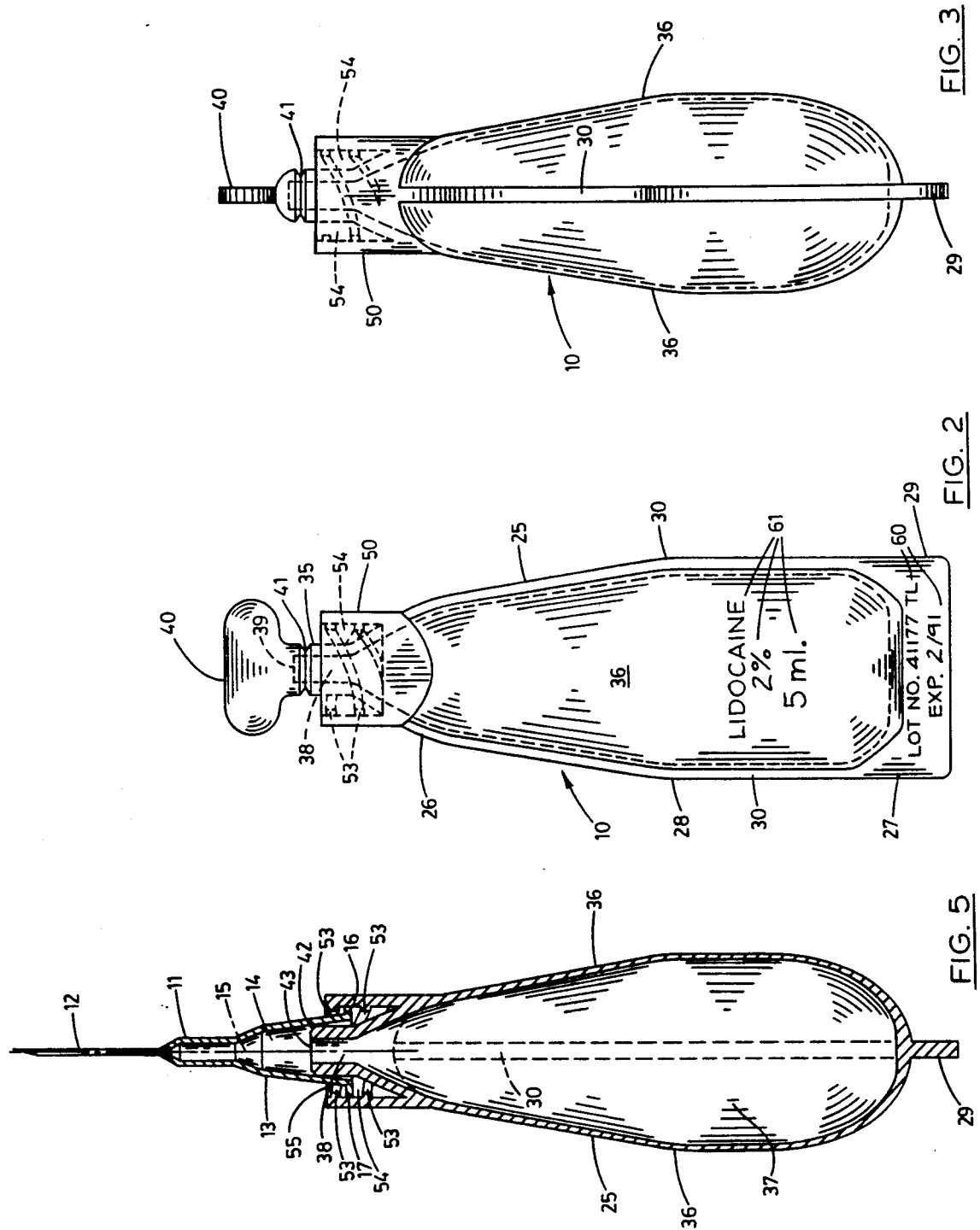

NON-REUSABLE DISPENSING APPARATUS

This is a continuation of copending application(s) Ser. No. 07/500,549 filed on Mar. 28, 1990 now abandoned.

BACKGROUND OF THE INVENTION

1. Field of the Invention

The present invention relates to a dispensing apparatus and more particularly to a dispensing apparatus which is particularly well suited to the application of fluid medication employing a needle as, for example, in the intradermal and subcutaneous injection of local anesthetics in the manner of a syringe.

2. Description of the Prior Art

The application of fluid substances, and more particularly fluid medications such as anesthetics applied with syringes, in such working environments as doctors' offices, hospitals, emergency facilities, other medical care facilities and the like is plagued by a host of difficulties which both detract from the ease and dependability with which such substances can be applied and from the safe and successful use of those substances. Thus, for example, while the use of syringes of a wide variety of types has long been known in the administering of fluid substances and while advances have been made in the construction and operation of such syringes, including the use of disposable syringes, such prior art devices are both inefficient to use, susceptible to improper or inexact usage and in some instances dangerous. Particularly, under emergency conditions or otherwise in those instances in which the circumstances of usage require expeditious procedures, such prior art devices are substantially less effective than would be desired.

In the case of conventional syringes, the user must locate a vial containing the required medication, attach a needle to the syringe, insert the needle into the vial, withdraw the plunger of the syringe until the desired volume of medication is received in the barrel of the syringe, remove the needle from the vial, recap the needle to remove it from the syringe, attach a new needle, expel any residual air within the barrel of the syringe from the syringe through the needle and subsequently administer the injection in the specified quantity. Subsequently, the syringe must be disposed of in accordance with specified disposal procedures. Depending upon the particular procedure performed, the needle is replaced after any contact with a nonsterile, or possibly nonsterile, environment. Thus, for example, the needle is replaced after withdrawal of the medication from the vial and prior to injection into the patient because the vial stopper may be nonsterile. In addition, typically, a smaller diameter needle is employed for the injection than for withdrawal of medication from the vial. These operations are not only time consuming and thus inefficient, but also conducive to error and thus hazardous, particularly under the tension of the circumstances under which the user must often operate.

In this regard, changing needles in conventional syringes requires that the user recap the needle. This is hazardous due to the risk of puncture by inadvertent contact with the needle. More over, conventional syringes are frequently used with multi-dose medication vials which can become contaminated and serve as a source of iatrogenic infection with such contagious agents as the Acquired Immune Deficiency Syndrome and Hepatitis viruses. Thus, the capability of conventional syringes to be refilled constitutes a means by which health hazards are perpetuated.

Therefore, it has long been known that it would be desirable to have a dispensing apparatus operable efficiently, safely and dependably to administer fluid substances such as medication under even the most aggravated emergency procedures requiring minimal manual dexterity by the user and therefore minimizing the opportunity for error while being as convenient as possible to leave the attention of the user available for other concerns.

SUMMARY OF THE INVENTION

Therefore, it is an object of the present invention to provide an improved dispensing apparatus having particular utility in the administering of fluid substances such as medication through a needle.

Another object is to provide such an apparatus which permits the administering of fluid medication in premeasured doses which remain sealed until immediately before the time of application and which can be employed in a sterile environment as well as in an environment in which only the fluid medication is sterilized.

Another object is to provide such an apparatus which does not require a syringe to be filled with the fluid medication to be administered prior to the injection and which cannot aspirate air back into the apparatus through the needle between injections.

Another object is to provide such an apparatus which is adapted to receive a wide variety of needle sizes and types, but which, as a preloaded apparatus, does not require recapping or the exchange of needles with the attendant hazards of this procedure prior to use.

Another object is to provide such an apparatus which is particularly well suited to use in emergency departments and other emergency situations wherein the rapid use thereof may be of critical importance.

Another object is to provide such an apparatus which is particularly well suited for the intradermal and subcutaneous injection of local anesthetics such as lidocaine and bupivicaine in selected procedures requiring local anesthesia, such as the closure of small to medium sized skin lacerations, the biopsy of skin lesions, minor plastic surgical procedures, and invasive procedures usually preceded by a local anesthetic injection.

Another object is to provide such an apparatus which can be employed as a disposable, single use, prefilled apparatus which can conveniently be stored and transported under virtually all types of conditions so as to be ready for use at anytime and without the hazards associated with conventional syringes and the like.

Further objects and advantages are to provide improved elements and arrangements thereof in an apparatus for the purpose described which is dependable, economical, durable and fully effective in accomplishing its intended purpose.

These and other objects and advantages are achieved, in the preferred embodiment of the dispensing apparatus of the present invention, wherein a container adapted to house a fluid to be dispensed in sealed relation has a member borne by the container for exposing the fluid for dispensing from the container through an opening and a mount borne by the container adjacent to the exposing member operable to secure an applying member, through which the fluid can be passed, in fluid transferring relation to the opening of the container.

BRIEF DESCRIPTION OF THE DRAWINGS

FIG. 1 is a perspective view of the dispensing apparatus of the present invention shown with a grasping portion thereof broken along a shear plane to expose a passage adapted to receive a needle assembly for use in administering the fluid medication contained therewithin.

FIG. 2 is a side elevation of the dispensing apparatus.

FIG. 3 is a side elevation of the dispensing apparatus rotated ninety (90) degrees from the position shown in FIG. 2.

FIG. 4 is a top plan view of the dispensing apparatus.

FIG. 5 is a longitudinal section taken from a position indicated by line 5—5 in FIG. 1.

DESCRIPTION OF THE PREFERRED EMBODIMENT

Referring more particularly to the drawings, the dispensing apparatus of the present invention is generally indicated by the numeral 10 in FIG. 1. The apparatus is adapted to be employed with a needle or similar device of any conventional type for the application of fluid substances such as medication, as will hereinafter be described. For purposes of illustrative convenience, the apparatus is shown in FIGS. 1 and 5 as employed in conjunction with a conventional needle assembly 11. The needle assembly has a tubular needle 12 mounted on a tubular mounting portion 13. A passage 14 extends entirely through the needle assembly along a longitudinal axis 15. A radial flange 16 extends outwardly about the tubular mounting portion to a peripheral edge 17. The flange is substantially radially disposed relative to the longitudinal axis 15.

The needle assembly 11 is typically enclosed by a removable plastic cap, not shown, which protects the needle until it is ready for use. The needle assembly and cap are usually sterilized and packaged in a paper and cellophane container.

The dispensing apparatus has a container or housing 25 which may generally be viewed as having an upper end portion 26 and an opposite lower end portion 27. The housing is preferably constructed of a synthetic plastic material of any suitable type and includes a rigid frame 28 which has a base flange 29 and lateral frame members 30. A tubular dispensing housing or neck 35 is mounted on the upper ends of the frame members 30 and is integral therewith. The housing 25 has a pair of sidewalls 36 which are mounted on and extend between the frame members 30 in substantially concavo-convex configurations so as to define a chamber 37 within the housing. The sidewalls are of thin plastic material, which in the manner of membranes, are capable of housing fluid medication within the chamber in fluid tight relation, but are quite flexible. Thus, the sidewalls do not possess the capability of springing back to an original configuration once deformed therefrom.

The neck 35 has a throat or passage 38 extending therethrough communicating with the chamber 37 and extending to a terminal end 39 visible in hidden lines in FIGS. 2 and 3. The neck has a grasping portion 40 and is circumscribed by a score line 41 effectively cutting into, but not through the neck. The score line defines a shear plane substantially right angularly related to the longitudinal axis 15 of a needle assembly 11 when stalled in position as shown in FIG. 5. The shear plane intersects the passage 38 just short of the terminal end 39. When the grasping portion 40 is broken off, as shown in FIG. 1, a beveled edge 42 is exposed circumscribing an opening 43 which allows fluid communication from the chamber 37, along the passage 38 and from the housing 25 through the opening 43.

A rigid collar 50 is mounted on the frame members 30 and having shoulders 51 integral with the sidewalls 36. The collar has an internal cylindrical passage 52. Within the cylindrical passage are spaced, substantially parallel helical ridges 53 defining grooves 54 between adjacent ridges. The collar has a mouth 55 communicating with the cylindrical passage 52.

For illustrative convenience, indicia 60 are formed or inscribed on the base flange 29 indicating the lot number and expiration date of the fluid medication housed in the chamber 37 of the housing 25. Indicia 61 are inscribed on one of the sidewalls 36 indicating the contents and volume of the fluid within the chamber 37.

OPERATION

The operation of the described embodiment of the present invention is believed to be readily apparent and is briefly summarized at this point. The dispensing apparatus 10 is stored in the condition shown in FIGS. 2 and 3 as a sealed container in which a premeasured quantity of fluid medication is contained. For example, the apparatus may contain five (5) milliliters of lidocaine in two percent (2%) solution which is indicated, for illustrative convenience, by the indicia 61 visible in FIGS. 1 and 2. Similarly, indicia 60 indicate the lot number and expiration date for the fluid medication. The dispensing apparatus can be constructed in any desired size, such as in three (3) milliliter and five (5) milliliter sizes by volume of its contents. Similarly the dispensing apparatus can be provided forms suited to the ultimate use thereof. Thus, the dispensing apparatus can be packaged in a clear cellophane plastic envelope with the entire apparatus sterilized and, alternatively, in an unpackaged form wherein only the fluid medication itself within the chamber 37 of the apparatus is sterilized.

When the dispensing apparatus is to be employed, a needle assembly 11 with the attached cap, not shown, is taken from its storage area and removed from its sterile package. With the dispensing apparatus supported in an upright position as shown in FIG. 5, the grasping portion 40 is grasped between thumb and fore finger as the user's other hand grips the frame members 30. Force is applied rotationally and laterally to the grasping portion to cause shearing of the neck 35 along the score line 41 to expose the opening 43. Since the frame members 30 are rigid and the apparatus is retained in an upright attitude, none of the fluid medication is expelled from the chamber 37.

Subsequently, grasping the needle cap enclosing the needle assembly 11, the tubular mounting portion 13 of the needle assembly is positioned about the neck and the radial flange 16 moved into the mouth 55 of the collar 50. The tubular mounting portion 13 is rotated by twisting the attached needle cap in a clockwise direction as shown in FIG. 1 so that the flange 16 has caused to travel in the grooves 54 of the collar drawing the tubular mounting portion downwardly into the cylindrical passage 52 and about the neck 35. Continued clockwise rotation of the attached needle cap causes the tubular mounting portion to be drawn into fluid transferring relation to the neck and a fluid tight seal is established between the beveled edge 42 of the neck and the inner surface of the tubular mounting portion 13 of the needle assembly about the opening 43. Thus, a fluid transferring relationship is established between the chamber 37, through the passage 38 of the neck 35 and through the passage 14 of the needle assembly 11. The dispensing apparatus and needle assembly are now ready for use. However, immediately before the dispensing apparatus and needle assembly are to be employed, the needle cap is removed from the needle assembly to expose the needle 12. Any residual air in the chamber 37 is then expelled through the needle by compression of the sidewalls 36.

The needle assembly is employed, for example, for intradermal or subcutaneous injection. Gripping the rigid frame members 30, sufficient pressure can be exerted along the longitudinal axis 15 of the needle assembly for the needle 12 to penetrate the skin in the desired location and manner. For example, this may be employed in selected procedures requiring local anesthesia, such as the closure of small to medium sized skin lacerations, biopsy of skin lesions, minor plastic surgical procedures, and invasive procedures usually preceded by local anesthetic injection.

Once the needle 12 is positioned in the desired position for administering of the fluid medication, the user presses the sidewalls 36 of the housing 25 toward each other to expel the fluid medication from the chamber at the desired rate along the passage 38 of the neck 35 and through the passage 14 of the needle assembly. Continued pressure on the sidewalls continues to force fluid medication from the chamber and such pressure is continued until the desired quantity of fluid medication is applied. Normally, this will involve expelling all of the fluid medication from the dispensing apparatus. However, depending upon the medication and procedure employed, typically, several injections are administered about the area so that the quantity is not consumed until several substantially equal injections have been made.

As previously noted, the sidewalls 36 are very thin and of a membrane like structure. Thus, they lack the rigidity which would cause them to rebound from a position once deformed. Since this is the case, the sidewalls cannot rebound in such a fashion as to aspirate air or other fluid back into the device between injections. Thus, this hazard is avoided.

When all of the fluid medication has been administered, the dispensing apparatus is disposed of in accordance with prescribed disposal procedures.

Therefore, the dispensing apparatus of the present invention is operable efficiently, safely and dependably to administer fluid substances such as medication under even the most aggravated emergency procedures requiring minimal manual dexterity by the user and therefore minimizing the opportunity for error while being as convenient as possible to leave the attention of the user available for other concerns.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

1. A dispensing apparatus comprising a substantially flat and substantially rigid frame having laterally spaced frame members; a housing mounted on and interconnecting said frame members at common end portions thereof; a pair of flexible membranes mounted on the frame in fluid tight relation and movable from each other to form a fluid tight chamber to receive a fluid to be dispensed; and means for selectively expelling said fluid from the chamber through the housing upon pressing the membranes toward each other and wherein said membranes are sufficiently thin so as not at any time to move from each other under the force of their own resiliency when released.

2. A dispensing apparatus comprising a substantially rigid frame having a pair of spaced lateral frame members interconnected at common end portions thereof by a lower frame member and so related to each other as to define a substantially common plane; a substantially rigid housing mounted on and interconnecting the lateral frame members in spaced relation to said lower frame member; a pair of concavo-convex membranes interconnecting said lateral frame members, lower frame member and housing to define therebetween a fluid tight chamber adapted to receive a fluid and being sufficiently thin to preclude rebounding outwardly once pressed inwardly; and means for selectively dispensing fluid through said housing from the chamber upon pressing said membranes toward each other whereby aspiration of air or other substances into the chamber is substantially precluded.

3. The apparatus of claim 2 wherein the membranes are sufficiently thin that they can be pressed toward each other to dispense fluid from the chamber through the housing until the membranes are disposed in substantially facing engagement and substantially all of the fluid has been dispensed from the chamber.

4. A dispensing apparatus comprising a substantially rigid frame having a pair of spaced lateral frame members interconnected at common end portions thereof by a lower frame member and so related to each other as to define a substantially common plane; a substantially rigid housing mounted on and interconnecting the lateral frame members in spaced relation to said lower frame member; a pair of concavo-convex membranes interconnecting said lateral frame members, lower frame member and housing to define therebetween a fluid tight chamber adapted to receive a fluid and being sufficiently thin to preclude rebounding outwardly once pressed inwardly; and means for selectively dispensing fluid through said housing from the chamber upon pressing said membranes toward each other whereby aspiration of air or other substances into the chamber is substantially precluded and wherein said dispensing means includes a passage extending through said housing from the chamber and a portion of said housing is adapted to be broken off along a plane intersecting said passage to establish fluid communication from said chamber through said housing to the exterior of said apparatus whereby the substantially rigid frame can be grasped in breaking off said portion of the housing to establish said fluid communication without pressing the membranes to dispense fluid through the passage from the chamber until desired.

5. A dispensing apparatus comprising a substantially rigid frame having a pair of spaced lateral frame members interconnected at common end portions thereof by a lower frame member and so related to each other as to define a substantially common plane; a substantially rigid housing mounted on and interconnecting the lateral frame members in spaced relation to said lower frame member, a pair of concavo-convex membranes interconnecting said lateral frame members, lower frame member and housing to define therebetween a fluid tight chamber adapted to receive a fluid and being sufficiently thin to preclude rebounding outwardly once pressed inwardly; means for selectively dispensing fluid through said housing from the chamber upon pressing said membranes toward each other whereby aspiration of air or other substances into the chamber is substantially precluded and wherein said dispensing means includes a passage extending through said housing from the chamber and a portion of said housing is adapted to be broken off along a plane intersecting said passage to establish fluid communication from said chamber through said housing to the exterior of said apparatus whereby the substantially rigid frame can be grasped in breaking off said portion of the housing to establish said fluid communication without pressing the membranes to dispense fluid through the passage from the chamber until desired; and a collar mounted on the frame about said housing operable to mount a needle assembly on the housing after said portion of the housing is broken off to establish fluid communication from the chamber, through the passage and from the apparatus through said needle assembly.

6. The apparatus of claim 5 wherein said membranes, when viewed in longitudinal section along a plane substantially right-angularly related to said substantially common plane defined by the lateral frame members, are very gradually convergent upon the housing and needle assembly so that the apparatus can be employed at a very shallow angle to horizontal.

* * * * *